United States Patent [19]
Perkins et al.

[11] Patent Number: 5,478,743
[45] Date of Patent: Dec. 26, 1995

[54] MICROBIALLY MEDIATED DEGRADATION OF NITROGEN-CONTAINING PHENOL COMPOUNDS BY SINGLE BACTERIAL ISOLATES

[75] Inventors: Richard E. Perkins; Janardhanan S. Rajan; Fateme S. Sariaslani, all of Newark, Del.

[73] Assignee: E. I. Du Pont de Nemours and Company, Wilmington, Del.

[21] Appl. No.: 212,459

[22] Filed: Mar. 11, 1994

[51] Int. Cl.$^6$ .............................. B09B 3/00; C12N 1/20; C12S 13/00
[52] U.S. Cl. ................. 435/262.5; 435/262; 435/252.1; 435/830; 588/203
[58] Field of Search ............................... 435/262, 262.5, 435/22, 252.1, 830; 588/203

[56] References Cited

U.S. PATENT DOCUMENTS

| | | |
|---|---|---|
| 4,535,061 | 8/1985 | Chakrabarty et al. .................. 435/253 |
| 5,085,998 | 2/1992 | Lebron et al. ........................... 435/262 |

FOREIGN PATENT DOCUMENTS

WO91/15440  10/1991  WIPO .............................. C05F 11/08

OTHER PUBLICATIONS

Sariaslani et al. "Microbial degradation of picric acid". Abstracts of Papers ACS207(1–2) 1994. Biosis Abstract 94:194078.

Lenke et al. "A Reductive Mechanism in the Aerobic Bacterial Degradation of Picric Acid". Abstr. Gen Mtg Am Soc Microb 92 (0) 1992. Biosis Abstract 92:400057.

Mendala, B., "A User Generated 'Custom' Library for the MIS", Technical Note #103, Jul. 1990, MIDI, 115 Barksdale Prof. Ctr., Newark, Del. 19711.

Thiele, J. et al, *Applied Environmental Microbiology*, 54(5), 1199–1202, May 1988.

"Anaerobic Bacteria Database", Version 3.8, Jan. 1994, MIDI, 115 Barksdale Prof. Ctr., Newark, Del. 19711.

Sasser, M., "Identification of Bacteria by Gas Chromatography of Cellular Fatty Acids", Technical Note #101, May 1990, MIDI, 115 Barksdale Prof. Ctr., Newark, Del. 19711.

Sasser, M., "'Tracking' A Strain Using Microbial Identification System", Technical Note #102, May 1990, MIDI, 115 Barksdale Prof. Ctr., Newark, Del. 19711.

Sasser, Myron (Ed.), *Fatty Acid Composition of Selected Seafoods*, MIDI, 115 Barksdale Prof. Ctr., Newark, Del. 19711, Copyright 1991, pp. 2–7, 9.

"Yeast/Actinomycetes/Fungi Database", Version 3.8, Jan. 1994, MIDI, 115 Barksdale Prof. Ctr., Newark, Del. 19711.

Wyman, J. F. et al, *Applied and Environmental Microbiology*, 37(2), 222–226, 1979.

Lenke, H. et al, *Applied and Environmental Microbiology*, 58(9), 2928–2932, 1992.

Gundersen, K. et al, *Acta. Agri. Scand.*, 6, 100–114, 1956.

Lenke, H. et al, *Applied and Environmental Microbiology*, 58(9), 2933–2937, 1992.

Hanne, L. F. et al, *Applied and Environmental Microbiology*, 59(10), 3505–3508, Oct. 1993.

Won, W. D. et al, *Applied Microbiology*, 27(3), 513–516, Mar. 1974.

Tabak, H. H. et al, *J. of Bacteriology*, 87(1), 910–919, 1964.

Westfall, B. B., *J. Pharmacol. Exp. Therap.*, 78, 386–393, 1943.

Kearney, P. C. et al, *Chemosphere*, 12(11/12), 1583–1597, 1983.

Erikson, D., *J. Bact.*, 41, 277–300, 1941.

Moore, F. W., *J. Gen. Microbiol.*, 3, 143–147, 1949.

Westerfield, W. W. et al, *J. Biol. Chem.*, 227, 379–391, 1957.

*Primary Examiner*—William H. Beisner
*Assistant Examiner*—Timothy J. Reardon

[57] ABSTRACT

The invention relates to Arthrobacter bacterial isolates capable of degrading picric acid and related compounds to the point where no aromatic ring-containing degradation products can be detected, as determined by HPLC profiles, UV-V spectrometry, analysis of total organic carbon and mineralization of $^{14}$C-picric acid. The isolates were derived from enrichments of bacterial cultures from waste sludge by successive subculturing into medium containing picric acid as the only carbon source.

9 Claims, No Drawings

5,478,743

MICROBIALLY MEDIATED DEGRADATION OF NITROGEN-CONTAINING PHENOL COMPOUNDS BY SINGLE BACTERIAL ISOLATES

FIELD OF INVENTION

The present invention relates to the microbially-mediated degradation of picric acid and other nitrogen substituted phenols by single bacterial isolates. More specifically, four bacterial isolates have been identified that have the ability to use picric acid as a carbon source and completely degrade picric acid to the level where no aromatic ring-containing degradation products can be detected.

BACKGROUND

Picric acid (2,4,6-trinitrophenol) is a compound used in a variety of industrial applications including the manufacture of explosives, aniline, color fast dyes, pharmaceuticals and in steel etching. Picric acid and ammonium picrate were first obtained as fast dyes for silk and wool. However, the unstable nature of picric acid was soon exploited for use as an explosive and explosive boosters. It is the primary component of blasting caps which are used for the detonation of 2,4,6-Trinitrotoluene (TNT). Because of its explosive nature, disposal of waste picric acid poses unique hazards not generally associated with other environmental toxicants.

Mounting public concern and increasing government regulations have provided the impetus for the development of a safe, effective means to remediate picric acid-contaminated environments. Past methods of disposing of munitions and other wastes containing picric acid have included dumping at specified land-fill areas, isolation in suitable, reinforced containers, land based deep-welling, dumping in deep water at sea and incineration. All of these methods carry some potential for harm to the environment. A more desirable disposal method might incorporate a chemical or enzymatic degradative process.

The metabolic reduction of organic nitrogen groups has been known for some time. Westfall (*J. Pharmacol. Exp. Therap.*, 78:386 (1943)) reported that liver, kidney and heart tissue are active in the reduction of trinitrotoluene, however, he was not able to identify the specific enzyme system responsible. Westerfield et al. (*J. Biol. Chem.*, 227:379 (1957)) further disclosed that purified xanthine oxidase is capable of reducing organic nitrogen groups and demonstrated that the molybdenum (Mo) co-factor was essential in the degradative process.

Microbial degradation of organic nitrogen compounds has been limited to a handful of organisms. Erickson (*J. Bact.*, 41:277 (1941)) reported that certain strains of Micromonospora were able to utilize picric acid and trinitro-resorcinol as a carbon source and Moore (*J. Gen. Microbiol.*, 3:143 (1949)) described two unspecified proactinomycetes as being capable of using nitrobenzene as a simultaneous source of carbon and nitrogen. Gundersden et al. (*Acta. Agric. Scand.*, 6:100 (1956)) described the metabolism of picric acid by Corynebacterium simplex which was isolated from soil as a 4,6-dinitro-2-methylphenol-degrading organism. Degradation was determined by measuring the amount of nitrite produced when the organism was contacted with an organic nitrogen compound. The extent of degradation and the identification of specific degradation products were not reported. Later, Wyman et al. (*Appl. Environ. Microbiol.*, 37(2):222 (1979)) found that a strain of Pseudomonas aeruginosa reduced picric acid to 2-amino- 4,6-dinitrophenol (picramic acid) under anaerobic conditions. Wyman further determined that degradation products from both picric and picramic acid produced by this strain demonstrated mutagenicity as assayed by the standard AMES test. Another *Pseudomonas sp.*, *P. putida*, has been shown to be able to use picric acid as a carbon source and achieve some bio-conversion of the compound to 1,3,5-trinitro benzene, 2,4,6-trinitroaldehyde, and 3,5-dinitrophenol. Kearney et al. (*Chemosphere*, 12 (11–12):1583 (1983)).

Most recently, *Rhodococcus erythropolis* has been identified as a picric acid degrading bacteria. Lenke et al. (*Appl. Environ. Microbiol.*, 58(9):2933 (1992)) teach that *R. erythropolis*, under aerobic conditions, can incompletely utilize picric acid as a nitrogen source producing nitrite and 2,4,6-trinitro-cyclohexanone, which cannot be degraded further.

In spite of the investigative activity in the area of microbial degradation of picric acid and other organic nitrogen compounds, there remain several difficulties to overcome before any of the above mentioned microbial systems can be used for the effective remediation of contaminated environments. All of the microbes investigated are isolated organisms and, although they show picric acid degrading activity in vitro, there is little evidence that these organisms will function under in situ conditions. Additionally, no organism or group of organisms has been isolated that demonstrates complete degradation of picric acid involving the opening of the aromatic ring. At present the art teaches that only partial degradation is possible and that some of the degradation products may also be harmful to the environment as mutagens. There remains a need, therefore, for an effective degradative process for picric acid and related compounds that will degrade those compounds completely and be effective in both the in vitro and in situ remediation of contaminated environments.

SUMMARY OF THE INVENTION

The present invention to provides a method of degrading nitrogen-containing phenol compounds comprising inoculating a bacterial isolate into a medium containing nitrogen-containing phenol compounds, the isolate utilizing the nitrogen-containing phenol compounds as a carbon source; and growing the isolate in the medium for a sufficient period of time until a decrease in the concentration of the nitrogen-containing phenol compounds and their aromatic ring-containing break-down intermediates is achieved. Even when picric acid is the sole carbon source, complete degradation of these compounds is achieved to the point where no aromatic ring-containing degradation products remain.

DETAILED DESCRIPTION OF THE INVENTION

The present invention relates to bacterial isolates capable of the complete degradation of picric acid and related compounds to the point where no aromatic ring-containing degradation products remain and the use of these isolates for the remediation of picric acid from contaminated environments.

As used herein, the following terms may be used for interpretation of the claims and specification.

The term "contaminated environments" refers to any environment contaminated with picric acid or related compounds. Typical contaminated environments may include, but are not limited to, soil, ground water, air, waste disposal sites, and waste streams.

The term "picric acid" refers to the compound 2,4,6-trinitrophenol.

The term "nitrogen-containing phenol compounds" refers to any phenol ring compound substituted with at least one $NO_2$ or $NH_2$ group or salts of the substituted compound. Picric acid is an example of such a compound. The phenol ring may also contain any other non-nitrogen chemical substitutions. Typical related compounds may include, but are not limited to, ammonium picrate, picramic acid, 2,4-dinitrophenol (2,4-DNP), 2,5-dinitrophenol (2,5-DNP), 2,6-dinitrophenol (2,6-DNP), 3-aminophenol, 2-aminophenol, 4-aminophenol, 2,4,6-trinitrotoluene, mononitrophenols, and nitroaromatics.

The term "complete degradation" refers to the degradation of picric acid and related compounds to a point where no aromatic ring-containing degradation products and no starting material may be detected.

The term "bacterial isolate" refers to a single bacterial species capable of mediating the complete degradation of picric acid and related compounds.

The biologically pure bacterial isolates of the present invention were selected for growth on medium containing picric acid as a carbon source. The picric acid degrading selected isolates were designated Nb, Nd, Nf, and FJ2-1A. All strains have been deposited with the American Type Culture Collection (ATCC) 12301 Parklawn Drive, Rockville, Md. 20852, U.S.A., under the terms of the Budapest Treaty and been designated with the accession numbers as indicated below:

| Arthrobucter Strain | ATCC number | Deposited |
|---|---|---|
| Nb | ATCC 55546 | 8 February 1994 |
| Nd | ATCC 55549 | 8 February 1994 |
| Nf | ATCC 55548 | 8 February 1994 |
| FJ2-1A | ATCC 55547 | 8 February 1994 |

Growth and Isolation of Bacterial Isolates

The isolates of the present invention were derived from enrichments of bacterial cultures isolated from the waste treatment facility of an industrial site and selected for the ability to use picric acid as a sole carbon source. The industrial site utilized a powdered activated carbon treatment (PACT) to process wastewater. The PACT process uses naturally occurring bacteria in an environment containing powdered activated carbon to consume organic wastes in the liquid phase of the wastewater.

Briefly, bacterial samples taken from the PACT facility were inoculated into a standard medium supplemented with picric acid as a carbon source. Concentrations of picric acid suitable for selecting organisms able to metabolize picric acid are preferably below 250 ppm where 125 ppm is most preferred.

Cultures were permitted to grow for about 100 h and then subcultured into fresh medium. Subculturing into fresh medium was continued for 11 months and then the cultures were either stored at −70° C. or tested for the ability to degrade picric acid and related compounds. After 11 months of subculturing, cells were diluted to obtain a suspension of cells in the range of 200–500 cfu/mL. Cells were then re-plated in the presence of picric acid and isolated colonies were picked from those plates that had shown degradation activity. This process produced the three bacterial isolates designated Nb, Nd, and Nf. FJ2-1A was produced in a similar manner, but from a sample obtained from an aniline/picric acid waste stream enrichment from using an inoculum from a waste treatment plant.

Classification of Bacterial Isolates

Individual bacterial isolates were grown on nutrient agar plates and analyzed by gas chromatography of cellular fatty acids. Actual identification of the microorganisms was done by Microbial ID Inc., (MIDI) Newark, Del. and the method for identification of microorganisms is described in MIDI technical note #101, 1990.

Briefly, cultures are grown on a standard trypticase soy broth base in the presence of brain-heart infusions with supplements. Following culture in broth, the microorganisms are subjected to saponification in sodium hydroxide, followed by methylation in HCl and methanol, and finally by fatty acid extraction into hexane and methyl tert-butyl ether. Gas chromatography of the extracted fatty acids reveals profiles of 9–20 carbon fatty acids in patterns typical of various genera and species of bacteria.

Analysis of the fatty acid profiles revealed that each of the strains possessed a unique pattern of bands or "fingerprint" that did not definitively match with any known microbial genera.

Nitrite Release Assay

One method for determining the amount of degradation of a nitrogen-containing compound is to analyze the amount of nitrite released during the degradation process. Methods for determining the amount of nitrite released from nitrogen-containing compounds are common and well known in the art. For example, Misko et al. (Anal. Biochem., 214, 11, (1993)) teach a fluorometric assay for the measurement of nitrite in biological samples which is designed to detect nitrite/nitrate. The method is based upon the reaction of nitrite with 2,3-diaminonaphthalene to form the fluorescent product, 1-(H)-naphthotriazole. Carson et al. (U.S. Government Report, DC/WRRC-42, W83-02296, OWRT-A-019-DC(1); Order No. PB83-180331, 31 pp. From: Gov. Rep. Announce. Index (U.S.) 1983, 83 (14), 3113) discuss the determination of nitrite and nitrate in water by reduction to ammonia followed by enzymic cycling involving the reduction of $NO_2-$ and/or $NO_3-$ to $NH_3$ with Devarda's metal while simultaneously trapping the released $NH_3$ gas with diluted aqueous HCl. Preferred for the present invention is the method described by Smibert et al. (Method I in Manual of Methods for General Bacteriology, Gerhardt, Murray, Costilow, Nester, Wood, Kreig & Phillips, Editors, p. 419 (1981)). This method involves the colorometric detection of nitrite by mixing a sample suspected of containing nitrite with N-1-naphthyl ethylenediamine HCL and sulfanilic acid with detection at 540 nm.

Mineralization Assays

An alternate method of determining enzymatic degradation of organic compounds is by mineralization assays involving radiolabled carbon. Compounds incorporating a radiolabel such as $^{14}C$ may be prepared by any means well known in the art and detection of $^{14}C$ labeled degradation products gives an indication of the extent and rate of degradation. For the purposes of the present invention, $^{14}C$-Picric Acid was obtained from New England Nuclear, (Boston, Mass.) and added to actively growing cultures of bacterial isolates. After a defined incubation time the incubation was terminated with the addition of 20% phosphoric acid (w/v) and the alkaline-trapping solution was placed in scintillation fluid for counting.

Total Organic Carbon Analysis

Measurement of the levels of total organic carbon (TOC) in culture media is another indication of the level of degradation of microbial carbon sources. In the present invention, levels of TOC were used to determine the amount and rate of picric acid degradation in cultures of bacterial isolates. Methods for the determination of TOC are common and well known in the art and any suitable method may be used. Sakamoto et al. (*Ultrapure Water*, 4(9), 24, 26–8, 30–1 (1987)) discuss a method for measuring TOC by wet oxidation and Heanes (*Commun. Soil Sci. Plant Anal.*, 15(10), 1191–213 (1984)) teaches the determination of total organic carbon in soils using chromic acid digestion followed by a spectrophotometric procedure. A review of current methods is provided by Haverty (*Ultrapure Water*, 1(2), 29–31 (1984)). For the purpose of the present invention a modification of standard methods was used. Briefly, the method involves introduction of samples into a column containing a TC catalyst where all of the carbon matter is oxidized to form carbon dioxide which is then detected by a non-dispersive infrared gas analyzer. The instrument is calibrated with a standard solution of potassium hydrogen phthalate as per the manufacturer's specification.

The following examples are meant to illustrate the invention, but should not be construed as limiting the invention in any way. The abbreviations used have the following meanings: "sec" means second (s), "min" means minute(s), "h" means hour(s), "d" means day(s), "mol" means mole(s), "m" means molar, "g" means gram(s), "mL" means milliliter, means Centigrade scale.

EXAMPLES

Materials and Methods

Identification of picric acid and related compounds was accomplished using the Hewlett Packard HPLC, model 1090 (Hewlett Packard, Valley Forge, Pa.) with an attached diode-array detector. HPLC mobile phases were obtained from the Millipore Corporation (Bedford, Mass.) and were used as recommended by the manufacturer for the separation of organic nitrogen compounds. Spectrophotometric determinations were performed using a Perkin Elmer lambda 5 spectrophotometer, (Perkin-Elmer Corp., Greenwich, Conn.).

$BaCl_2\cdot 2H_2O$ for use in barium precipitation studies was obtained from Fischer Scientific (Pittsburgh, Pa.), and was reagent grade. Scintillation fluid used in scintillation counting was NEN 989 (New England Nuclear, Boston, Mass.). Picric acid was obtained from Aldrich (cat. #31,928-7) as a 1% solution in water. $^{14}C$ Picric acid (ring-$^{14}C(U)$) was obtained from New England Nuclear, (Boston, Mass.) (1.06 μCi; specific activity 8.7 μCi/mmol; in 0.9 mL ethanol, FW 229.11).

EXAMPLE 1

Isolation and Identification of Bacterial Isolates

Isolation of Crude Bacterial Mixtures

Samples of sludge which contained microorganisms were recovered from aerators at an industrial waste treatment facility. A 5 mL PACT sample was inoculated into 25 mL of minimal medium (Table 1) containing 1.25 mL picric acid (1% solution in water). The culture was maintained at 30° C. with shaking for 100 h. The culture, 5 mL, was withdrawn and subcultured in 25 mL minimal medium supplemented with 1.25 mL picric acid as described above. A sample of cultures that have been continuously subcultured for 11 months was used. These cultures had been grown at 30° C. and had been subcultured every 100 h. The final subculture (after 11 months) contained $2\times 10^9$ cells/mL. Cells from this subculture were diluted with minimal medium to obtain a suspension of cells in the range of 200–500 cfu/mL. A tenth of a milliliter of the suspension was plated on minimal agar plates containing 100 ppm of picric acid. Isolated colonies were picked from those plates that showed degradation activity. These colonies were streaked on fresh plates and the isolates were monitored for their ability to degrade picric acid. Single colonies were picked once again, to insure purity, to finally obtain the isolates described in these studies, designated Nb, Nd, and Nf. Isolate FJ2-1A was isolated in a similar manner where the source of picric acid in the isolation media was an aniline waste stream containing 2500 ppm picric acid. Colonies of isolates grown on R2A agar plates and tested for the ability to utilize picric acid in liquid cultures.

TABLE 1

| Minimal Medium (1) | | Yeast Extract | Trace Elements (3) | |
| --- | --- | --- | --- | --- |
| Compound | Weight (g) | (2) (10% Soln.) | Compound | Weight (g) |
| $K_2HPO_4$ | 6 | | $MgSO_4\cdot 7H_2O$ | 2 |
| $KH_2PO_4$ | 4 | | $CaCl_2$ | 0.4 |
| $NH_4Cl$ | 3.2 | | $MnSO_4$ | 0.08 |
| | | | $FeSO_4\cdot 7H_2O$ | 0.05 |
| | | | $Na_2MoO_4\cdot 3H_2O$ | 0.15 |
| (Make to 1 liter with double distilled water, pH 7.2–7.3) | | | (Make to 100 mL with double distilled water and add 1 ml conc. HCl) | |

To 1 L of (1) add 5 mL of (2) and 10 mL of (3).
Add 100–1000 ppm of picric acid.

EXAMPLE 2

Growth of Bacterial Isolates

Growth Conditions

Degradation of picric acid was analyzed both from cultures of actively growing cells in log phase or from cells in stationary or resting phase.

Log Phase Cultures

All isolates were grown for 72 h at 30° C. with shaking, on MMY (Table 2) containing 250 ppm picric acid and were inoculated (5% inoculum) into fresh MMY containing either 250 or 1000 ppm picric acid. Picric acid was added from a stock solution of 9500 ppm picric acid prepared by using a 10,000 ppm standard solution which was neutralized to pH 7.5 with 1N NaOH and sterilized by filtration.

Samples (2 mL) were drawn aseptically at given time intervals, centrifuged at 8000 g for 10 min. to remove cell mass and the supernatant was analyzed for picric acid by measuring absorbance at 354 nm. All dilutions for optical density measurements (OD at 600 nm), as needed, were carried out in 0.1N HCl. A calibration curve (shown below as Table 3) for picric acid and other nitrophenol compounds.

All dilutions were carried out in 0.1N HCl and an assay sensitive in the range of 1–16 ppm was developed.

TABLE 2

Minimal Minerals Yeast extract medium (MMY)

| | g/L |
|---|---|
| Sodium phosphate (monobasic, monohydrate) | 0.6 |
| Potassium phosphate (dibasic) | 1.8 |
| Ammonium sulfate | 1.5 |
| Yeast extract | 0.5 |
| pH | 7.2 |
| Mineral solution (stock) | 10 mL/L* |
| *Final concentration of minerals in the medium | |
| $MgCl_2$ $6H_2O$ | 200 mg |
| $CaCl_2$ $2H_2O$ | 40 mg |
| $MnCl_2$ $4H_2O$ | 8 mg |
| $Na_2MoO_4$ $2H_2O$ | 15 mg |
| $FeCl_2$ $6H_2O$ | 5 mg |

Resting Cell Cultures

Each of the isolates were grown on MMY (1 liter containing 250 ppm of picric acid) for 72 h, and harvested by centrifugation at 6000 g. The cell pellets (1 g/L dry wt.) were resuspended in 250 mL of MMY medium. Two 25 mL aliquots were withdrawn for dry weight measurements. The remaining 200 mL suspension was dispensed into eight 125 mL flasks, at 25 mL per flask and picric acid was added to the desired concentration (500 ppm). The flasks were incubated in rotary shaker (275 rpm) and samples were withdrawn for picric and total organic carbon (TOC) analysis. For experiments demonstrating the ability of the isolates to use picric acid as a sole carbon source, the above growth protocol was modified only by the removal of the yeast extract from the MMY growth media.

EXAMPLE 3

HPLC Analysis of Picric Acid Degradation

HPLC Analysis and Detection

Identification of picric acid and related compounds was accomplished using the Hewlett Packard HPLC, model 1090 (Hewlett Packard, Valley Forge, Pa.) with an attached diode-array detector. Separations of picric acid and break-down products were carried out on a Supelcosil LC8 column (Supelco, PA)—25 cm long, 4.6 mm diameter with 5 micron packing and column guard employing a gradient with two mobile phases. The first mobile phase consisted of 20% HPLC grade methanol with 0.1% acetic acid. The second mobile phase, was deionized water with 0.1% acetic acid. The elution gradient began with holding the first mobile phase, (20% methanol with 0.1% acetic acid) for 2 min. followed by an increase to 90% over 35 min. Total flow was 1 mL/min. Using this protocol, data were collected for three different wavelengths of 354, 280 and 450 nm (reference at 550) and analyzed for sample peak area. As can be seen by the data in Table 3, elution time for picric acid was 2.4±0.5 min. Minimum detectable concentration of picric acid was 5 ppm as determined by a known standard.

Samples of cell-free medium were analyzed by a diode-array detector using a sample wavelength of 354 nm and a reference wavelength of 550 nm. Using this protocol it was possible to separate and quantify picric acid.

TABLE 3

Elution time for nitrophenol standards.

| Chemical standard (50 ppm) | Elution time (min.) |
|---|---|
| Picric acid | 2.4 ± 0.5 |
| 2,4-Dinitrophenol | 5.3 ± 0.5 |
| 2,6-Dinitrophenol | 4.9 ± 0.4 |
| 2-Nitrophenol | 8.1 ± 0.4 |
| 4-Nitrophenol | 6.8 ± 0.4 |
| 2-Nitro-4-aminophenol | 13.4 ± 0.4 |
| 2-Amino-4-nitrophenol | 6.6 ± 0.5 |

Total Organic Carbon (TOC) Analysis

Total organic carbon remaining in the medium at various time intervals were carried out using a Shimadzu Total Organic Carbon Analyzer (TOC-5050) (Shimadzu Scientific Instruments, MD). The method involves introduction of 25–100 μL of samples into a column containing a TC Catalyst where all of the carbon matter is oxidized to form carbon dioxide. The TC combustion tube is filled with TC catalyst and heated to 680° C. Carrier gas (purified air) is supplied into this tube at about 150 mL/min. The carrier gas with the combustion product ($CO_2$) is dehumidified, scrubbed to remove any halogens and is detected by a non-dispersive infrared gas analyzer. The instrument is calibrated with a standard solution of potassium hydrogen phthalate, as per the manufacturers specification.

Picric Acid Degradation

Bacterial isolates Nb, Nd, Nf, and FJ2-1A were grown for log phase growth as described above. Control media containing no inoculum of cell were incubated under identical conditions. Samples were removed at 0, 12, and 24 h and analyzed by HPLC and by spectrophotometry at 354 nm, 280 nm and 450 nm for the presence of picric acid and other degradation products. Results are summarized in Tables 4–7.

TABLE 4

Isolate FJ2-1A

| Time (h) | Area under @ Picric | 354 nm Total | Area under @ Picric | 280 nm Total | Area under @ Picric | 450 nm Total |
|---|---|---|---|---|---|---|
| 0 | 18824 | 18964 | 3135 | 3634 | 2752 | 2771 |
| 12 | 0 | 417 | 0 | 949 | 0 | 9 |
| 24 | 0 | 457 | 0 | 1385 | 0 | 0 |

Notes:
"@ Picric" - Corresponds to area under peak at the elution time for Picric acid of 2.65 ± 0.15 min.
Cell dry weight at start = 1.14 g/L.
Picric acid concentration at start = 385 ppm.

TABLE 5

Isolate Nb

| Time (h) | Area under @ Picric | 354 nm Total | Area under @ Picric | 280 nm Total | Area under @ Picric | 450 nm Total |
|---|---|---|---|---|---|---|
| 0 | 21897 | 22030 | 3688 | 4282 | 3407 | 3500 |
| 12 | 557 | 1102 | 118 | 1339 | 355 | 508 |
| 24 | 183 | 675 | 53 | 1269 | 0 | 277 |

TABLE 5-continued

Isolate Nb

| Time (h) | Area under @ Picric | 354 nm Total | Area under @ Picric | 280 nm Total | Area under @ Picric | 450 nm Total |
|---|---|---|---|---|---|---|

Notes:
"E Picric" - Corresponds to area under peak at the elution time for Picric acid of 2.65 ± 0.15 min.
Cell dry weight at start = 1.09 g/L.
Picric acid concentration at start = 450 ppm.

TABLE 6

Isolate Nd

| Time (h) | Area under @ Picric | 354 nm Total | Area under @ Picric | 280 nm Total | Area under @ Picric | 450 nm Total |
|---|---|---|---|---|---|---|
| 0 | 22121 | 22145 | 3748 | 4512 | 3693 | 4000 |
| 12 | 256 | 2240 | 77 | 1952 | 0 | 2373 |
| 24 | 173 | 1572 | 0 | 1726 | 0 | 1662 |

Notes:
"E Picric" - Corresponds to area under peak at the elution time for Picric acid of 2.65 ± 0.15 min.
Cell dry weight at start = 1.03 g/L.
Picric acid concentration at start = 450 ppm.

TABLE 7

Isolate Nf

| Time (h) | Area under @ Picric | 354 nm Total | Area under @ Picric | 280 nm Total | Area under @ Picric | 450 nm Total |
|---|---|---|---|---|---|---|
| 0 | 22243 | 22419 | 3753 | 4109 | 3233 | 3240 |
| 12 | 37 | 453 | 40 | 865 | 0 | 16 |
| 24 | 14 | 428 | 34 | 844 | 0 | 14 |

Notes:
"E Picric" - Corresponds to area under peak at the elution time for Picric acid of 2.65 ± 0.15 min.
Cell dry weight at start = 1.172 g/L.
Picric acid concentration at start = 450 ppm.

Samples monitored at 280 nm and 450 nm demonstrate a similar decline in picric acid concentration. Because many aromatics are visualized at 280 nm, this data present strong evidence that degradation of picric acid involves destruction of the aromatic ring.

In order to determine the changes in total organic carbon (TOC) of media as picric acid is degraded, bacterial isolates Nb, Nf and FJ2-1A were first grown for resting cell growth in MMY media containing yeast extract as described above. Control media containing no inoculum of cells were incubated under identical conditions. Samples were removed at 0, 18, 26, and 44 h and analyzed by HPLC and by spectrophotometry at 354 nm for the presence of picric acid. TOC analysis was accomplished using the protocol described above. Results are shown in Tables 8 and 9.

TABLE 8

Time course for degradation of picric acid and total organic carbon with resting cells

| Time (h) | Nb Picric (ppm) | TOC (ppm) | Nf Picric (ppm) | TOC (ppm) | FJ2-1A Picric (ppm) | TOC (ppm) |
|---|---|---|---|---|---|---|
| 0 | 850 | 393 ± 6 | 850 | 410 ± 18 | 850 | 380 ± 45 |
| 18 | 17 | 228 ± 15 | 320 | 272 ± 15 | 18 | 235 ± 53 |
| 26 | 29 | 234 ± 4 | 171 | 232 ± 4 | 15 | 209 ± 35 |
| 44 | 25 | 243 ± 9 | 27 | 191 ± 9 | 17 | 191 ± 12 |

Notes:
Cell dry weight at start
Nb      1092 mg/L
Nf      1172 mg/L
FJ2-1A  1140 mg/L

TABLE 9

TOC values at 44 h for control medium containing only yeast extract at 0.05%

| Strain | Picric Acid | TOC |
|---|---|---|
| Nb | 0 | 108 ppm ± 12 |
| Nf | 0 | 116 ppm ± 8 |
| FJ2-1A | 0 | 92 ppm ± 3 |
| Yeast extract (no cells) | 0 | 176 ppm ± 6 |
| Complete medium | 850 ppm | 412 ± 15 |

Notes:
Picric acid contains 31.44% carbon - based on 6 C/mole, i.e., 850 ppm corresponds to 267 ppm of TOC.

As is evident from the data in Tables 8 and 9, disappearance of picric acid is directly correlated with a decrease in TOC in the media, suggesting aromatic ring destruction by the degradation process.

In order to demonstrate that the bacterial isolates are able to use picric acid as a sole carbon source and to track the carbon degradation pathway, Nb, Nd, Nf, and FJ2-1A were grown for resting cell growth in MMY media containing no yeast extract as described above. The only carbon source in the media was 250 ppm picric acid. Control media containing no inoculum of cells were incubated under identical conditions. Samples were removed at 0 and 75 h and analyzed by HPLC and by spectrophotometry at 354 nm for the presence of picric acid. TOC analysis was accomplished using the protocol described above. Results are shown in Table 10.

TABLE 10

Yield of biomass from picric as the sole carbon source

| | Time: 0 h | | Time: 75 h | | Biomass |
|---|---|---|---|---|---|
| Strain | Picric (ppm) | TOC (ppm) | Picric (ppm) | TOC (ppm) | Yield $Y_{x/s}$ (g/g) |
| FJ2-1A | 250 | 79 | 0 | 7 | 0.162 |
| Nb | 250 | 79 | 0 | 7 | 0.260 |
| Nd | 250 | 79 | 0 | 8 | 0.308 |
| Nf | 250 | 79 | 0 | 9 | 0.368 |

As can be seen by the data in Table 10, all of the picric acid is degraded and it appears that a significant amount is converted into biomass as opposed to $CO_2$.

EXAMPLE 4

Degradation of Non-Picric Acid Nitrophenols

Example 4 illustrates that at least one of the bacterial isolates, FJ2-1A, is able to degrade structural analogs of picric acid, i.e., nitrophenols lacking either one or two nitro groups.

Cells were grown in two liters of minimal medium modified to obtain a better buffering capacity, that is, to counter the lowering of pH due to $NO_2^-$ release. The components of the modified minimal medium are given below in Table 11.

TABLE 11

| Minimal Minerals Yeast extract medium (MMY) | |
| --- | --- |
|  | g/L |
| Sodium hydrogen phosphate (monobasic) | 1.8 |
| Potassium hydrogen phosphate (dibasic) | 5.4 |
| Ammonium sulfate | 1.5 |
| Yeast extract | 0.5 |
| pH | 7.2 |
| Mineral solution (stock) | 10 mL/L* |
| *Final concentration of minerals in the medium | |
| $MgCl_2$ $6H_2O$ | 200 mg |
| $CaCl_2$ $2H_2O$ | 40 mg |
| $MnCl_2$ $4H_2O$ | 8 mg |
| $Na_2MoO_4$ $2H_2O$ | 15 mg |
| $FeCl_2$ $6H_2O$ | 5 mg |

FJ2-1A cells were inoculated (5% inoculum) into the modified minimal medium containing 500 ppm of picric acid and grown for 60 h. The cells were harvested by centrifugation at 5000 g and resuspended in 500 mL of minimal medium to obtain cell density of 1 g/L (dry weight basis). To 50 mL aliquots were added various nitrophenols as described below in Table 12

TABLE 12

| Flask # | Compound | Concentration |
| --- | --- | --- |
| 1 | Picric acid | 500 ppm |
| 2 | Picric acid | 500 ppm |
|  | and 2,4-dinitrophenol | 250 ppm |
| 3 | 2,4-dinitrophenol | 250 ppm |
| 4 | Picric acid | 500 ppm |
|  | and 2,6-dinitrophenol | 250 ppm |
| 5 | 2,6-dinitrophenol | 250 ppm |
| 6 | Picric acid | 500 ppm |
|  | and 2-nitrophenol | 250 ppm |
| 7 | 2-nitrophenol | 250 ppm |
| 8 | Picric acid | 500 ppm |
|  | and 4-nitrophenol | 250 ppm |
| 9 | 4-nitrophenol | 250 ppm |

The remaining 50 mL were used for dry weight determinations.

Samples were obtained at time 0, 6, 12 and 24 h and analyzed by HPLC as described above. The results have been summarized in Table 13.

TABLE 13

| Nitrophenol | Degradation rates (ppm/h/g cells) |
| --- | --- |
| Picric acid (2,4,6-trinitrophenol) | 70–80 |
| 2,4-dinitrophenol | 46–60 |
| 2,6-dinitrophenol | 3–5 |
| 2-nitrophenol | 2–5 |

TABLE 13-continued

| Nitrophenol | Degradation rates (ppm/h/g cells) |
| --- | --- |
| 4-nitrophenol | 8–12 |

It is clear from the data in Table 13 that all of the structural analogs of picric acid containing aromatic rings were degraded to some extent by isolate FJ2-1A.

EXAMPLE 5

Mineralization of Picric Acid by Bacterial Isolates

Reagents for Studying Picric Acid Mineralization $CO_2$-free Water

De-ionized $H_2O$ was boiled for 15 min in an Erlenmeyer flask with a beaker inverted on top of flask, followed by rapid cooling to room temperature by placing on ice. The $CO_2$ free water was used to prepare NaOH and $BaCl_2$ solutions.

1N NaOH 4.0 g NaOH was added to 100 mL $CO_2$-free water in a volumetric flask.

Barium Chloride Solution 0.89M $BaCl_2$-$2H_2O$ was prepared consisting of 21.73 g to 100 ml $CO_2$-free water (volumetric flask), and 0.5M barium.

Basal Salt Medium (BSM)

BSM consisted of 50 mM potassium phosphate, pH 7; mM ammonium sulfate, 2 nM ferric sulfate, and 1 mM magnesium chloride.

$^{14}C$ Picric Acid Stock Solution 0.96 mL of $^{14}C$-picric acid (8.7 µCi/mmol) was added to 25 mL of 5000 ppm picric acid to give a working solution of 4.5 µCi/mL with a specific activity of 202 µCi/mmol.

$^{14}C$—$Na_2CO_3$:

$^{14}C$—$Na_2CO_3$ was obtained from New England Nuclear (Boston, Mass.) 250 µCi, having a specific activity of 8 mCi/mmol. The $^{14}C$—$Na_2CO_3$ was dissolved in 5 mL of $dH_2O$ (pH 10). 1 mL of this stock solution was transferred to 9 mL of $dH_2O$ (pH 10) to make a working stock (0.05 µCi/0.1 mL).

Obtaining the Cell Mass Required for the Mineralization Studies

In order to obtain sufficient bacteria for picric acid mineralization studies, each of the four strains Nb, Nd, Nf, and FJ2-1A (10 mL inoculum) were grown in 500 mL capacity flasks containing 100 mL of the minimal medium plus 0.05% of yeast extract. 100 ppm picric acid was added to each flask (final concentration). Cultures were incubated at 28° C. while shaking at 150 rpm. After 24 h of growth, cells were harvested (Sorval Centrifuge, SS34 rotor, for 10 min. at 10,000 rpm). The pellets were washed twice with 20 mL of 50 mM potassium phosphate buffer (pH 7). The cells were resuspended in the same buffer to a density of 55 Klett unit (using filter #66).

$^{14}C$-Picric Acid Mineralization Experiment

Cells (0.5 mL of the suspension prepared as above) were added to 20 mL capacity scintillation vials equipped with a center well containing a piece of fluted filter paper (1×5 cm). NaOH (0.4 mL, of a 1N solution) was added to the center well at zero time. 4.4 mL of the 50 mM phosphate buffer (see above) and 100 µL of the $^{14}C$-picric acid were added to the vials. Control vials contained 4.13 mL of the buffer and 270

μL of formaldehyde; 0.5 mL of cell suspension; and 100 μL of the $^{14}$C-picric acid. Vials were sealed and left on the shaker (180 rpm) for 24 h. After 24 h, 0.5 mL of 20% phosphoric acid (w/v) was added to the vials to stop the reaction and drive the $CO_2$ out of the solution. Vials were left on the shaker for 1 h. The center wells were placed in 15 mL of scintillation fluid (formula 989,New England Nuclear) and were counted for 5 min. Duplicates were set up for each experiment and the counts obtained were averaged. Three different sets of experiments were performed for each strain.

Results of these experiments are summarized in Table 14 below. These results indicate mineralization of $^{14}$C-picric acid (17–25%) by these isolates to produce $^{14}CO_2$. The following amounts of $^{14}CO_2$ were produced from various isolates:

TABLE 14

| Strain | % $^{14}CO_2$ formed | |
| --- | --- | --- |
| FJ2-1A | 17.86 | Av. = %17.97 |
| FJ2-1A | 19.87 | |
| FJ2-1A | 16.18 | |
| Nd | 23.48 | Av. = % 24.03 |
| Nd | 23.07 | |
| Nd | 25.54 | |
| Nb | 20.64 | Av. = % 25.74 |
| Nb | 22.13 | |
| Nb | 34.46 | |
| Nf | 25.83 | |
| Nf | 13.05 | Av. = % 20.86 |
| Nf | 23.70 | |

Barium Precipitation Assay

To positively determine that the radioactive material released in the mineralization studies was indeed $^{14}$C—$CO_2$, barium precipitate analysis of the NaOH trapped $CO_2$ was done according to the following protocol.

Serum bottles (total bottle volume 162 mL) containing a 12×75 mm culture tube to hold $CO_2$ trapping agent (2.5 mL 1N NaOH) were used. Bottles were sealed with crimp top caps with Teflon-lined septa. The following were added to the serum bottles: 1 mL of cell suspension, 8.8 mL Buffer, and 200 μL of $^{14}$C-picric acid. Killed controls were set up as follows: 1 mL cell suspension, 0.4 mL 37% formaldehyde, 8.4 mL KPi, and 200 μl $^{14}$C-picric acid. Cells were prepared as described above (see picric acid mineralization).

Reaction bottles were incubated in the dark with shaking (150 rpm) at 25° C.±2° C. for 24 h then 1 mL 20% phosphoric acid (w/v) was added. The bottles were shaken at 150 rpm for 1 h. The NaOH trapping agent was collected and a 1 mL aliquot of the NaOH trapping agent was added to either 0.5 mL $CO_2$-free water or 0.5 mL barium chloride solution in a Sarstedt 1.5 mL screw-cap microfuge tube (final barium conc. 0.167M). The tubes were shaken by hand periodically to mix the solution and let stand at room temp for 30 min. The tubes were then centrifuged for 5 min. at 14,000 rpm (Eppendorf 5414 C microcentrifuge). 1 mL of the supernatant was collected and added to 15 mL scintillation fluid with care being taken not to disturb the barium pellet.

Results of the barium precipitation are shown in Table 15 below.

TABLE 15

| Removal of $^{14}CO_2$ by Barium precipitation | |
| --- | --- |
| Strain | % DPM removed from $CO_2$ trap |
| FJ2-1A | 99.5 |
| Nf | 99.3 |
| Nb | 99.1 |
| Nd | 98.8 |

As can been seen by the data in Table 15, virtually all of the counts were precipitated by the $BaCl_2$ indicating that all of $^{14}$C product of the mineralization experiments was indeed $^{14}CO_2$.

EXAMPLE 6

Release of Nitrite during Degradation of Picric Acid by Bacterial Isolates

Example 6 demonstrates picric acid degradation by bacterial isolates by measuring the amount of nitrite released during picric acid degradation.

Reagents necessary for the assay of nitrite are listed below.

A—1.5N HCl

B—0.02% N-1-Naphthyl ethylenediamine HCL in 50 mL of 1.5NHCl

C—1% Sulfanilic acid

D—Standard=Stock solution of sodium nitrite (1 g/L)

Test Reagent=a mixture of equal volume of (B) and (C)

Nitrite Assay

Nitrite was assayed essentially as described by Smibert et al. (Method I in Manual of Methods for General Bacteriology, Gerhardt, Murray, Costilow, Nester, Wood, Kreig & Phillips, Editors p. 419 (1981)).

Briefly, an assay mixture (4 mL) was prepared consisting of de-ionized $H_2O$ (1.9 mL); Standard (0.1 mL) and test reagent (2 mL). The mixture was allowed to incubate for 15–20 min. to allow for any color change, periodically mixing vigorously by vortexing. A pink color denotes the presence of nitrite. The assay control consisted of de-ionized $H_2O$ (2 mL) and the test reagent (2 mL) and was treated in parallel with the sample. After incubation, the absorbance was read at 540 nm.

The four bacterial isolates, Nb, Nd, Nf, and FJ2-1A were grown up in 250 mL Erlenmeyer flasks containing picric acid 100 or 200 ppm in minimal medium (with or without yeast extract 0.05% final conc.). Cultures were incubated in the dark with shaking (150 rpm) at 28° C. for various time periods. No cell and killed controls were also incubated. Nitrite release was measured as described above. Data illustrating the amount of nitrite released during picric acid degradation for each isolate is given below in Table 16.

TABLE 16

| Strain | % Picric Acid-N released as Nitrite |
| --- | --- |
| FJ2-1A | 56.09 |
| Nd | 51.14 |
| Nb | 48.38 |
| Nf | 49.76 |

As can be seen by the data in Table 16 all of the bacterial isolates release nitrite from picric acid. Table 17 shows the stoichiometry of picric acid consumed and nitrite released for FJ2-1A.

TABLE 17

| Strain | μmole picric acid consumed | μmole Nitrite released | mole NO$_2$/mole picric acid |
|---|---|---|---|
| FJ2-1A | 423.3 | 1138.8 | 2.69 |

EXAMPLE 7

Classification of Bacterial Isolates by Fatty Acid Composition

Cultures of the four bacterial isolates, Nb, Nd, Nf, and FJ2-1A were streaked on R2A (Difco) medium and individual colonies were picked and re-plated on the same medium to confirm the individuality of the colonies. Each colony was subjected to analysis of fatty acid composition according to the method described in MIDI technical note #101, 1990 (Microbial ID Inc., (MIDI) Newark, Del.).

Cultures were grown on a standard trypticase soy broth base in the presence of brain-heart infusions with supplements. Following culture in broth, the microorganisms were subjected to saponification in sodium hydroxide, followed by methylation in HCl and methanol, and finally fatty acid extraction into hexane and methyl tert-butyl ether. Gas chromatography of the extracted fatty acids reveals profiles of 9–20 carbon fatty acids in patterns typical of various genera and species of bacteria. Each of the fatty acid profiles was compared against a database of similar profiles containing 200 bacterial genera. Information detailing the profiles contained in the database, the types of fatty acids analyzed, as well as descriptions of the software analysis is available from MIDI, Inc. (Newark, Del.) and is contained in MIDI technical notes 101, 102 and 103. The fatty acid composition analysis revealed that each of the four isolates possessed a unique pattern or "fingerprint" illustrated below in Tables 18–20.

TABLE 18

FJ2-1A

| RT | Area | Ar/Ht | Response | ECL | Name | % |
|---|---|---|---|---|---|---|
| 1.586 | 39933000 | 0.080 | | 7.012 | SOLVENT PEAK | |
| 1.837 | 1276 | 0.029 | | 7.559 | | |
| 1.900 | 1031 | 0.027 | | 7.696 | | |
| 7.727 | 1909 | 0.040 | 0.973 | 14.621 | 15:0 ISO | 2.60 |
| 9.022 | 817 | 0.042 | 0.952 | 15.457 | 16:1 ISO H | 1.09 |
| 9.294 | 10390 | 0.042 | 0.949 | 15.625 | 16:0 ISO | 13.79 |
| 9.599 | 2602 | 0.047 | 0.945 | 15.815 | 16:1 CIS 9 | 3.44 |
| 9.897 | 3502 | 0.043 | 0.942 | 15.999 | 16:0 | 4.61 |
| 10.961 | 4949 | 0.044 | 0.931 | 16.630 | 17:0 ISO | 6.45 |
| 11.118 | 1125 | 0.043 | 0.930 | 16.723 | 17:0 ANTEISO | 1.46 |
| 11.233 | 1470 | 0.044 | 0.929 | 16.791 | 17:1 CIS 9 | 1.91 |
| 11.349 | 6823 | 0.046 | 0.928 | 16.859 | 16:0 ISO 20H | 8.85 |
| 11.988 | 2722 | 0.047 | 0.923 | 17.232 | 16:0 20H | 3.51 |
| 12.296 | 1514 | 0.046 | 0.920 | 17.410 | 17:0 10METHYL | 1.95 |
| 12.681 | 1304 | 0.046 | 0.918 | 17.632 | 18:0 ISO | 1.67 |
| 12.917 | 17749 | 0.047 | 0.916 | 17.768 | 18:1 CIS 9 | 22.75 |
| 13.009 | 1411 | 0.047 | 0.916 | 17.821 | Sum In Feature 7 | 1.81 |
| 13.099 | 2869 | 0.049 | 0.915 | 17.873 | 17:0 ISO 20H | 3.67 |
| 13.319 | 3498 | 0.065 | 0.914 | 18.000 | 18:0 | 4.47 |
| 14.000 | 12520 | 0.046 | 0.911 | 18.394 | TBSA 18:0 10METHYL | 15.95 |

TABLE 19

NB

| RT | Area | Ar/Ht | Response | ECL | Name | % |
|---|---|---|---|---|---|---|
| 1.586 | 39448000 | 0.079 | | 7.012 | SOLVENT PEAK | |
| 1.764 | 2986 | 0.024 | | 7.400 | | |
| 6.320 | 798 | 0.038 | 0.995 | 13.618 | 14:0 ISO | 0.60 |
| 6.814 | 817 | 0.037 | 0.984 | 13.999 | 14:0 | 0.61 |
| 7.659 | 3355 | 0.039 | | 14.571 | | |
| 7.733 | 5605 | 0.039 | 0.968 | 14.621 | 15:0 ISO | 4.09 |
| 7.867 | 1738 | 0.039 | 0.966 | 14.712 | 15:0 ANTEISO | 1.27 |
| 8.293 | 690 | 0.036 | 0.960 | 15.000 | 15:0 | 0.50 |
| 9.031 | 1055 | 0.043 | 0.951 | 15.457 | 16:1 ISO H | 0.76 |
| 9.303 | 62477 | 0.042 | 0.948 | 15.626 | 16:0 ISO | 44.67 |
| 9.607 | 3599 | 0.046 | 0.945 | 15.814 | 16:1 CIS 9 | 2.56 |
| 9.904 | 3726 | 0.048 | 0.942 | 15.998 | 16:0 | 2.65 |
| 10.092 | 5246 | 0.042 | | 16.110 | | |
| 10.635 | 4397 | 0.053 | 0.936 | 16.431 | 16:0 10METHYL | 3.10 |
| 10.970 | 2525 | 0.044 | 0.934 | 16.629 | 17:0 ISO | 1.78 |
| 11.127 | 13784 | 0.044 | 0.933 | 16.722 | 17:0 ANTEISO | 9.70 |

TABLE 19-continued

NB

| RT | Area | Ar/Ht | Response | ECL | Name | % |
|---|---|---|---|---|---|---|
| 11.243 | 6316 | 0.045 | 0.932 | 16.791 | 17:1 CIS 9 | 4.44 |
| 11.599 | 1406 | 0.045 | 0.930 | 17.002 | 17:0 | 0.99 |
| 11.939 | 968 | 0.052 | | 17.198 | | |
| 12.306 | 10362 | 0.046 | 0.927 | 17.409 | 17:0 10METHYL | 7.24 |
| 12.691 | 1534 | 0.055 | 0.925 | 17.631 | 18:0 ISO | 1.07 |
| 12.926 | 12315 | 0.048 | 0.924 | 17.767 | 18:1 CIS 9 | 8.59 |
| 13.331 | 1026 | 0.053 | 0.923 | 18.000 | 18:0 | 0.71 |
| 14.011 | 6715 | 0.046 | 0.922 | 18.394 | TBSA 18:0 10METHYL | 4.67 |

TABLE 20

ND

| RT | Area | Ar/Ht | Response | ECL | Name | % |
|---|---|---|---|---|---|---|
| 1.586 | 40026000 | 0.080 | | 7.008 | SOLVENT PEAK | |
| 1.764 | 1661 | 0.024 | | 7.396 | | |
| 6.816 | 663 | 0.041 | 0.984 | 14.000 | 14:0 | 0.79 |
| 7.734 | 2844 | 0.039 | 0.968 | 14.621 | 15:0 ISO | 3.35 |
| 7.868 | 927 | 0.038 | 0.966 | 14.712 | 15:0 ANTEISO | 1.09 |
| 9.303 | 34806 | 0.041 | 0.948 | 15.625 | 16:0 ISO | 40.09 |
| 9.609 | 1525 | 0.042 | 0.945 | 15.815 | 16:1 CIS 9 | 1.75 |
| 9.906 | 2106 | 0.044 | 0.942 | 15.999 | 16:0 | 2.41 |
| 10.631 | 1477 | 0.065 | 0.936 | 16.428 | 16:0 10METHYL | 1.68 |
| 10.971 | 2449 | 0.042 | 0.934 | 16.630 | 17:0 ISO | 2.78 |
| 11.127 | 16263 | 0.044 | 0.933 | 16.722 | 17:0 ANTEISO | 18.44 |
| 11.243 | 4307 | 0.047 | 0.932 | 16.791 | 17:1 CIS 9 | 4.88 |
| 11.598 | 902 | 0.049 | 0.930 | 17.001 | 17:0 | 1.02 |
| 12.306 | 2678 | 0.046 | 0.927 | 17.409 | 17:0 10METHYL | 3.02 |
| 12.691 | 1437 | 0.048 | 0.925 | 17.631 | 18:0 ISO | 1.62 |
| 12.927 | 11821 | 0.046 | 0.924 | 17.767 | 18:1 CIS 9 | 13.28 |
| 13.330 | 758 | 0.049 | 0.923 | 18.000 | 18:0 | 0.85 |
| 14.011 | 2647 | 0.046 | 0.922 | 18.394 | TBSA 18:0 10METHYL | 2.96 |
| 14.708 | 1214 | 0.073 | | 18.798 | | |

TABLE 21

NF

| RT | Area | Ar/Ht | Response | ECL | Name | % |
|---|---|---|---|---|---|---|
| 1.586 | 39983000 | 0.080 | | 7.010 | SOLVENT PEAK | |
| 1.764 | 2375 | 0.024 | | 7.398 | | |
| 1.835 | 653 | 0.032 | | 7.553 | | |
| 1.899 | 497 | 0.031 | | 7.693 | | |
| 6.321 | 620 | 0.035 | 0.997 | 13.619 | 14:0 ISO | 0.19 |
| 6.814 | 1657 | 0.040 | 0.985 | 13.998 | 14:0 | 0.50 |
| 7.659 | 2157 | 0.037 | | 14.571 | | |
| 7.734 | 39161 | 0.039 | 0.969 | 14.622 | 15:0 ISO | 11.55 |
| 7.867 | 6527 | 0.039 | 0.967 | 14.712 | 15:0 ANTEISO | 1.92 |
| 8.218 | 938 | 0.041 | | 14.950 | | |
| 8.293 | 2993 | 0.041 | 0.960 | 15.000 | 15:0 | 0.87 |
| 9.303 | 55434 | 0.042 | 0.948 | 15.626 | 16:0 ISO | 15.99 |
| 9.608 | 5888 | 0.046 | 0.945 | 15.815 | 16:1 CIS 9 | 1.69 |
| 9.904 | 12943 | 0.045 | 0.942 | 15.998 | 16:0 | 3.71 |
| 10.092 | 4827 | 0.043 | | 16.110 | | |
| 10.634 | 7420 | 0.056 | 0.935 | 16.430 | 16:0 10METHYL | 2.11 |
| 10.706 | 2028 | 0.042 | 0.935 | 16.473 | Sum In Feature 5 | 0.58 |
| 10.971 | 24261 | 0.044 | 0.933 | 16.630 | 17:0 ISO | 6.89 |
| 11.128 | 56780 | 0.044 | 0.932 | 16.722 | 17:0 ANTEISO | 16.10 |
| 11.243 | 17971 | 0.045 | 0.931 | 16.790 | 17:1 CIS 9 | 5.09 |
| 11.598 | 12392 | 0.045 | 0.929 | 17.001 | 17:0 | 3.50 |
| 11.781 | 1472 | 0.043 | | 17.106 | | |
| 11.940 | 3470 | 0.045 | | 17.198 | | |
| 12.308 | 19064 | 0.046 | 0.925 | 17.410 | 17:0 10METHYL | 5.37 |
| 12.411 | 1162 | 0.046 | 0.925 | 17.470 | 18:1 ISO H | 0.33 |

TABLE 21-continued

<u>NF</u>

| RT | Area | Ar/Ht | Response | ECL | Name | % |
|---|---|---|---|---|---|---|
| 12.691 | 1682 | 0.057 | 0.923 | 17.632 | 18:0 ISO | 0.47 |
| 12.926 | 40447 | 0.047 | 0.922 | 17.767 | 18:1 CIS 9 | 11.35 |
| 13.019 | 3178 | 0.049 | 0.922 | 17.821 | Sum In Feature 7 | 0.89 |
| 13.329 | 6124 | 0.049 | 0.921 | 18.000 | 18:0 | 1.72 |
| 14.011 | 30394 | 0.047 | 0.919 | 18.395 | TBSA 18:0 10METHYL | 8.50 |
| 14.635 | 2403 | 0.059 | 0.918 | 18.756 | Sum In Feature 8 | 0.67 |
| 14.704 | 5116 | 0.048 | | 18.796 | | |
| 17.349 | 1458 | 0.070 | | 20.330 | | |
| 19.063 | 1430 | 0.064 | | 21.327 | | |
| 19.237 | 1791 | 0.062 | | 21.428 | | |

What is claimed is:

1. A method of degrading an isolated sample containing tri-nitro phenol compounds comprising:
   (a) isolating a sample from a contaminated environment comprising tri-nitro phenol compounds;
   (b) inoculating a bacterial isolate into said sample, said bacterial isolate utilizing said tri-nitro phenol compounds as a carbon source resulting in the production of break-down intermediates; and
   (c) growing said bacterial isolate in said sample for a sufficient time period and under conditions sufficient for said growth until a decrease in the concentration of said tri-nitro phenol compounds and their break-down intermediates is achieved;
   wherein the bacterial isolate is selected from the group of Arthrobacter species consisting of ATCC 55546, ATCC 55547, ATCC 55548 and ATCC 55549.

2. A method of degrading an isolated sample containing tri-nitro phenol compounds comprising:
   (a) isolating a sample from a contaminated environment comprising tri-nitro phenol compounds;
   (b) inoculating a bacterial isolate into said sample, said bacterial isolate utilizing said tri-nitro phenol compounds as a carbon source resulting in the production of break-down intermediates; and
   (c) growing said bacterial isolate in said sample for a sufficient time period and under conditions sufficient for said growth until a decrease in the concentration of said trinitro phenol compounds and their break-down intermediates is achieved, wherein the bacterial isolate is selected from the group of Arthrobacter species consisting of ATCC 55546, ATCC 55547; ATCC 55548 and ATCC 55549; and
   wherein said decrease in concentration is at least 50%.

3. The method of claim 1 wherein the tri-nitro phenol compounds are the sole source of carbon utilized by the bacterial isolate for growth.

4. The method of claim 1 wherein one of the tri-nitro phenol compounds is picric acid.

5. A biologically pure Arthrobacter bacterial isolate identified as ATCC 55546.

6. A biologically pure Arthrobacter bacterial isolate identified as ATCC 55547.

7. A biologically pure Arthrobacter bacterial isolate identified as ATCC 55548.

8. A biologically pure Arthrobacter bacterial isolate identified as ATCC 55549.

9. A biologically pure bacterial isolate as in any one of claims 5–8 which completely degrades picric acid.

* * * * *